(12) United States Patent
Feistel (10) Patent No.: US 10,329,554 B2
(45) Date of Patent: Jun. 25, 2019

(54) SYSTEM AND METHOD FOR SEQUESTERING SUBSTANCES IN BULK LIQUIDS

(71) Applicant: WAVESENSE, INC., Irvine, CA (US)

(72) Inventor: Christopher Feistel, Irvine, CA (US)

(73) Assignee: WAVESENSE, INC., Irvine, CA (US)

( * ) Notice: Subject to any disclaimer, the term of this patent is extended or adjusted under 35 U.S.C. 154(b) by 327 days.

(21) Appl. No.: 15/345,271

(22) Filed: Nov. 7, 2016

(65) Prior Publication Data

US 2018/0127741 A1  May 10, 2018

(51) Int. Cl.

| C12N 15/10 | (2006.01) |
|---|---|
| B01L 3/00 | (2006.01) |
| B03C 1/28 | (2006.01) |
| G01N 1/40 | (2006.01) |
| B03C 1/01 | (2006.01) |
| B03C 1/30 | (2006.01) |

(52) U.S. Cl.
CPC .......... *C12N 15/1013* (2013.01); *B01L 3/508* (2013.01); *B01L 3/50825* (2013.01); *B03C 1/01* (2013.01); *B03C 1/288* (2013.01); *B03C 1/30* (2013.01); *G01N 1/405* (2013.01); *B01L 2200/0668* (2013.01); *B01L 2300/042* (2013.01); *B01L 2300/046* (2013.01); *B01L 2300/0832* (2013.01); *B01L 2400/043* (2013.01); *B03C 2201/18* (2013.01); *B03C 2201/26* (2013.01)

(58) Field of Classification Search
CPC ............................ C12N 15/1013; B01L 3/508
See application file for complete search history.

(56) References Cited

U.S. PATENT DOCUMENTS

| 6,479,302 B1 | 11/2002 | Dremel |
|---|---|---|
| 2006/0223178 A1 | 10/2006 | Barber et al. |
| 2007/0166835 A1 | 7/2007 | Bobrow et al. |
| 2010/0047766 A1 | 2/2010 | Barrault et al. |
| 2010/0233675 A1 | 9/2010 | Barrault et al. |
| 2012/0132593 A1 | 5/2012 | Murthy et al. |
| 2012/0270331 A1 | 10/2012 | Achrol et al. |
| 2016/0184737 A1 | 6/2016 | Oscarsson et al. |

OTHER PUBLICATIONS

Ali, A, et al., Assessment of circulating tumor cells (CTCs) in prostate cancer patients with low-volume tumors, Pathol. Int., 2010, 60 (10): 667-72.
Blanker, M, et al., Voided Volumes: Normal Values and Relation to Lower Urinary Tract Symptoms in Elderly Men, A Community-Based Study, Urology, 2001, 57: 1093-1099.
Chen, Peng, et al., Inkjet-Print Micromagnet Array on Glass Slides for Immunomagnetic Enrichment of Circulating Tumor Cells, Annals of Biomedical Engineering, Aug. 20, 2015, 44 (5): 1710-1720.
Chen, Peng, et al., Microscale Magnetic Field Modulation for Enhanced Capture and Distribution of Rare Circulating Tumor Cells, Scientific Reports, Mar. 4, 2015, 5: 8745.
Cohen, SJ, et al., Relationship of circulating tumor cells to tumor response, progression-free survival, and overall survival in patients with metastatic colo-rectal cancer, J. Clin. Oncol. 2008, 26 (19), 3213-21.
Hayes, DF, et al., Is There a Role for Circulating Tumor Cells in the Management of Breast Cancer?, Clin. Cancer Res., 2008, 14 (12): 3646-50.
Pachmann, K., et al., Monitoring the Response of Circulating Epithelial Tumor Cells to Adjuvant Chemotherapy in Breast Cancer Allows Detection of Patients at Risk of Early Relapse, J. Clin. Oncol., 2008, 26: 1208-1215.
Desitter, I.; et al., A New Device for Rapid Isolation by Size and Characterization of Rare Circulating Tumor Cells, Anticancer Research, 2011, 31 (2): 427-442.
Doornum, G.J.J., et al., Detection of Chlamydia trachomatis Infection in Urine Samples from Men and Women by Ligase Chain Reaction, Journal of Clinical Microbiology, Aug. 1995, vol. 33, No. 8, 2042-2047.
Esmaeilsabzail, H, et al., Detection and isolation of circulating tumor cells: principles and methods, Biotechnol. Adv., 2013, 31 (7): 1063-84.
Hoshino, Kazunori, et al., Microchip-based immunomagnetic detection of circulating tumor cells, Lab on a Chip, Oct. 2011, 11 (20): 3449-3457.
Hoshino, Kazunori, et al., Computational Analysis of Microfluidic Immunomagnetic Rare Cell Separation from a Particulate Blood Flow, Analytical Chemistry, May 15, 2012, 84 (10): 4292-4299.
Huang, Yu-Yen, et al., Screening and Molecular Analysis of Single Circulating Tumor Cells Using Micromagnet Array, Scientific Reports, Nov. 5, 2015, 5: 16047.
Huang, Yu-yen, et al., Immunomagnetic nanoscreening of circulating tumor cells with a motion controlled microfluidic system, Biomedical Microdevices, Oct. 30, 2012, 15 (4): 673-681.
Luecke, Klaus, et al., The Gilupi Cellcollector as an in vivo tool for circulating tumor cell enumeration and molecular characterization in lung cancer patients, ASCO Annual Meeting Proceedings, 2015, vol. 33, No. 15 suppl.

(Continued)

*Primary Examiner* — Taeyoon Kim
*Assistant Examiner* — Tiffany M Gough
(74) *Attorney, Agent, or Firm* — Stetina Brunda Garred and Brucker (57) ABSTRACT

Systems and methods for detecting and sequestering target analytes in a fluid sample. The system comprises a bulk specimen reservoir for receiving a liquid sample, along with paramagnetic materials operative to selectively bind to the target analyte of interest. A vertex is interconnected with the bulk specimen reservoir to define a specimen chamber assembly to which a magnetic chamber is deployed about the vertex portion thereof and operative to sequester the magnetic particles, as well as any analyte of interest bound thereto, within the interior of the vertex. Once sufficient time is allowed for mixing and allowing the magnetic capsule to sufficiently retain the magnetic particles within the vertex, the vertex is disconnected from the specimen reservoir and the paramagnetic materials retained therein analyzed to determine the presence of the analyte of interest.

10 Claims, 7 Drawing Sheets

(56) References Cited

OTHER PUBLICATIONS

Marrinucci, D, et al., Circulating tumor cells from well-differentiated lung adenocarcinoma retain cytomorphologic features of primary tumor type, Archives of Pathology &, Laboratory Medicine, Sep. 2009, 133 (9): 146871.

Pachmann, K.; et al., Quantification of the response of circulating epithelial cells to neoadjuvant treatment for breast cancer: a new tool for therapy monitoring, Breast Cancer Res., 2005, 7:, R975-979.

Paterlini-Brechot, P, et al., Circulating tumor cells (CTC) detection: Clinical impact and future directions, Cancer Lett., 2007, 253 (2): 180-204.

Peng, Chen, et al., Multiscale immunomagnetic enrichment of circulating tumor cells: from tubes to microchips, Lab on a Chip, 2014, 14: 446-458.

Saucedo-Zeni, Nadia; et al., A novel method for the in vivo isolation of circulating tumor cells from peripheral blood of cancer patients using a functionalized and structured medical wire, International Journal of Oncology, 2012, 41 (4): 1241-1250.

Scheumann, N, et al., Numeration and molecular characterization of circulating tumor cells in lung cancer patients using the Gilupi Cellcollector, an effective in vivo device for capturing CTCS, Annals of Oncology, 2015, 26: 14.

Wang, Huiqiang, et al., Optical Detection and Virotherapy of Live Metastatic Tumor Cells in Body Fluids with Vaccinia Strains, PLoS ONE, Sep. 2013, 8 (9): e71105.

Wang, ZP, et al., Identification and characterization of circulating prostate carcinoma cells, Cancer, 2000, 88 (12): 278795.

Yu, M, et al., RNA sequencing of pancreatic circulating tumour cells implicates WNT signalling in metastasis, Nature, 2012, 487 (7408): 510-3.

Yu, M.; et al., Circulating tumor cells: approaches to isolation and characterization, The Journal of Cell Biology, 2011, 192 (3): 373-382.

Nagrath, Sunitha, et al., Isolation of rare circulating tumour cells in cancer patients by microchip technology, Nature, Dec. 2007, 450 (7173): 1235-1239.

Attard, G, et al., Characterization of ERG, AR and PTEN gene status in circulating tumor cells from patients with castration-resistant prostate cancer, 2009, Cancer Res. 69 (7): 2912-8.

Bethel, Kelly; et al., Fluid phase biopsy for detection and characterization of circulating endothelial cells in myocardial infarction, Physical Biology., Jan. 9, 2014, 11 (1): 016002.

Elsheikh, T., Urine Cytology Challenges and Pitfalls, www.ahn.org/sites/default/files/file/elsheikh-2.

Panteleakou, Z, et al., Detection of circulating tumor cells in prostate cancer patients: methodological pitfalls and clinical relevance, Mol Med., 2009, 15 (3-4): 101-14.

Nieva, J, et al., High-definition imaging of circulating tumor cells and associated cellular events in non-small cell lung cancer patients: a longitudinal analysis, Physical Biology, Feb. 2012, 9 (1): 016004.

SYSTEM AND METHOD FOR SEQUESTERING SUBSTANCES IN BULK LIQUIDS

CROSS-REFERENCE TO RELATED APPLICATIONS

Not Applicable

STATEMENT RE: FEDERALLY SPONSORED RESEARCH/DEVELOPMENT

Not Applicable

BACKGROUND

The present invention relates to systems and methods for identifying, separating and isolating target analytes or impurities suspected of being present in a liquid sample but in quantities typically too low to detect using prior art mechanisms. The invention further relates to systems and methods for the detection and sequestration of target analytes based in part on volume reduction of the sample where such particles are believed to be present, coupled with the magnetic separation of such targeted analytes.

Separation techniques that are capable of identifying specific biological macromolecules, cells, and the like (collectively referred to as "biological particles") are well-known in the art and used extensively for analytical and purification purposes in biological research, biomedical technology and diagnostic applications. In general, such separation techniques rely upon one or more physical and/or chemical properties of the target biological particle sought to be identified so as to capture or isolate the target particle at a fixed position or area. Among the properties that have been utilized to facilitate the identification and isolation of biological particles include density, size, hydrophobicity, electrical charge and surface chemical groups operative to react and bind with other materials and/or immunological agents. Exemplary of such techniques include: centrifugation, which can be used to separate cellular components based upon their relative density; liquid chromatography, which involves passing a sample over a packed column of particles that have a defined surface chemistry and/or porosity that are operative to interact and retain the target biological particles; and gel electrophoresis, which is operative to separate biological macromolecules via the application of an electric field, that in turn affects the mobility of such molecules to move through the gel in one or two dimensions based upon the charge-to-mass ratio of the macromolecule of interest.

Also frequently applied in separation techniques is microfluidics, which operate on the principle of manipulating and controlling fluids, usually in the range of microliters to picoliters, in networks of channels of different diameter, usually ranging from 5 to 500 µm. Such reduced dimensions are selectively chosen so that particles of a fluid sample, or particles suspended in the fluid sample, become comparable in size with the microfluidic apparatus itself. On such reduced scale, fluids are directed, mixed, separated or otherwise manipulated to attain multiplexing, automation, and high-throughput systems. Microfluidics can allow for the analysis and use of samples of much lesser volumes, as well as correspondingly lesser amounts of any chemicals and reagents utilized therewith, and have the capacity to both process and analyze samples with minor sample handling.

In addition to such techniques, there have further been utilized systems and methods for detecting biological macromolecules and cells of interest using magnetic particles that are operative to interact with an applied magnetic field. In a typical application, magnetic particles will carry a ligand on the surfaces thereof that enables the particle to bind specifically to a target biological macromolecule. In application, such magnetic particles are added to a sample, and allowed to bind with the macromolecule of interest, thereafter which a magnetic field is applied that enables the magnetic particles and the bound macromolecules of interest to be separated from the rest of the sample. The captured macromolecule of interest is then measured by detection, such as fluorescence-based emission, and can be used in conjunction with flow cytometric analysis.

References that are exemplary of the state of the art with respect to the separation of biological macromolecules, cells and the like are set forth in the following issued patent and published patent applications:

U.S. Pat. No. 6,479,302 B1, entitled METHOD FOR THE IMMUNOLOGICAL DETERMINATION OF AN ANALYTE, issued Nov. 12, 2002 to Bernd Dremel;

United States Published Patent Application No. 2006/0223178 A1, entitled DEVICES AND METHODS FOR MAGNETIC ENRICHMENT OF CELLS AND OTHER PARTICLES, published Oct. 5, 2006 to Barber et al.;

United States Published Patent Application No. 2007/0166835 A1, entitled MULTIPLEX ASSAYS USING MAGNETIC AND NON-MAGNETIC PARTICLES, published Jul. 19, 2007 to Mark N. Bobrow;

United States Published Patent Application No. 2010/0047766 A1, entitled ANALYTE MANIPULATION AND DETECTION, published Feb. 25, 2010 to Barrault et al.;

United States Published Patent Application No. 2010/0233675 A1, entitled ANALYTE MANIPULATION AND DETECTION, published Sep. 16, 2010 to Barrault et al.;

United States Published Patent Application No. 2012/0132593 A1, entitled SYSTEMS AND METHODS FOR MAGNETIC SEPARATION OF BIOLOGICAL MATERIALS, published May 31, 2012 to Murthy et al.;

United States Published Patent Application No. 2012/0270331 A1, entitled MICROFLUIDIC SYSTEM AND METHOD FOR AUTOMATED PROCESSING OF PARTICLES FROM BIOLOGICAL FLUID, published Oct. 25, 2012 to Achrol et al.; and United States Published Patent Application No. 2016/0184737 A1, entitled NEW PROCESS AND SYSTEM FOR MAGNETIC SEPARATION, published Jun. 30, 2016 to Oscarsson et al.

The teachings of all of the foregoing are expressly incorporated herein by reference.

Notwithstanding the general effectiveness of the aforementioned methodologies often times the target analyte of interest, despite being present in a sample, is in quantities too low to detect using such prior art techniques. In this regard, such methods are often unable to concentrate or enrich a sample sufficiently to allow analysis of rare components that may be present in the sample. In addition, such methodologies can result in unacceptable losses of rare components, as can occur through inefficient separation or degradation of the biological particles of interest. Perhaps well-known and exemplary of the shortcomings associated with finding rare and difficult to identify analytes is the identification of circulating tumor cells (CTC), as explained in more detail at https:en.wikipedia.org/wiki/Circulating_tumor_cell on the Wikipedia website.

Figure 1:
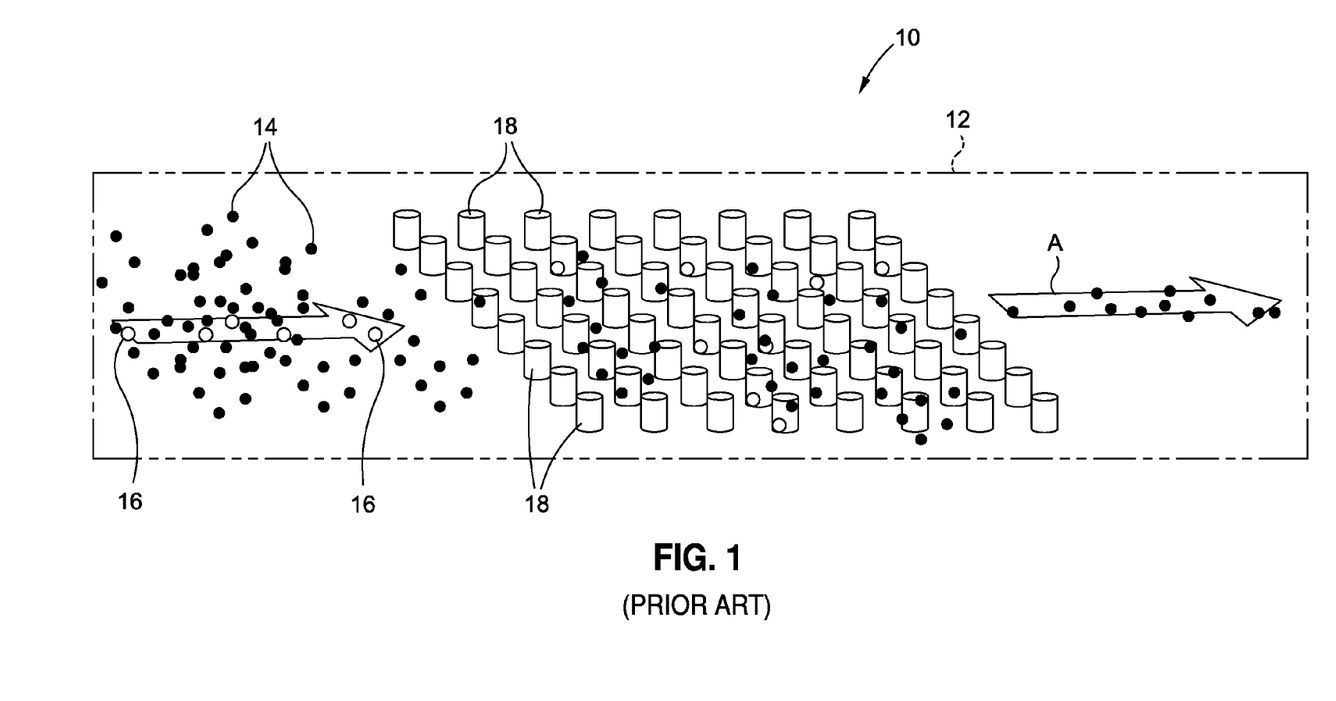
FIG. 1 illustrates a representative prior art microfluidic method of separating a target analyte from a bulk fluid specimen.
Figure 2:
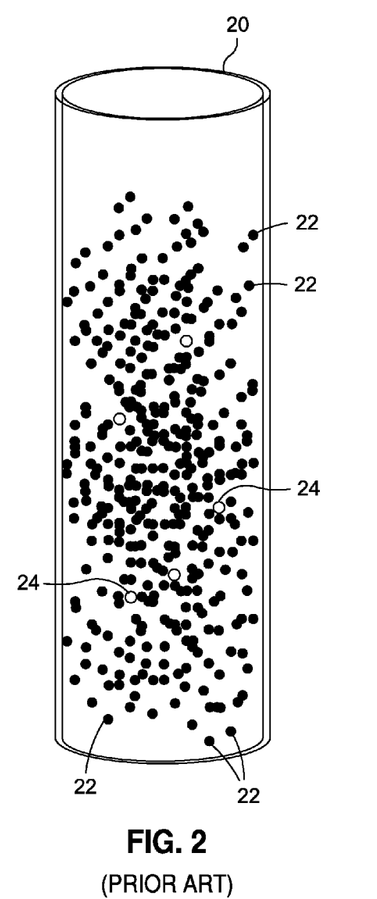
FIG. 2 illustrates a container with bulk fluid specimen containing multiple analytes and target analytes binding paramagnetic particles.

For example, microfluidic flow through design, as shown in FIG. 1, is well-recognized as being inefficient and slow. As discussed above, the typical microfluidic design involves a layout 10 defining a pathway 12 through which a fluid sample flows, as indicated by the direction A. Multiple analytes 14 present in a fluid sample, as well as target analytes 16 sought to be detected, are caused to flow past barriers, flow-channels, grids, and the like, represented as 18, whereby the physical barriers provided by such structure 18 are operative to selectively control the rate and position by which the analytes flow through the system. The best method takes 15 hours to process 7.5 mL of whole blood and yields only a 40% recovery. These methods are not suitable for commercial scaling applications such as screening patients for cancer cells. See, e.g., Miyamoto, D. T., et. al. Nat. Rev. Clin. Oncol. 11, 401-412 (2014). "Studies have shown that there are several advantages to using the HB-Chip over the CTC chip to capture circulating tumor cells. First, the HB-Chip has the capacity to filter blood at higher flow rates than the CTC chip while still maintaining efficiency. At low flow rates, about 0.12 mL/hr, the cell capture efficiency for the HB-Chip averages 79%, while flat chamber devices, like the CTC chip, average 29%. When flow rates reach up to 0.48 mL/hr, the HB-chip manages a cell capture efficiency of more than 40%, while the average efficiency for a CTC chip at this rate is around 8%."

With respect to the drawbacks associated with magnetic separation techniques, there is shown in FIGS. 2-5 how such magnetic separation techniques are ineffectual to effectively draw out and isolate the target biological particle/macromolecule of interest. As referenced above, the ability to couple paramagnetic particles to target analytes of interest are well-known in the art, and as shown FIG. 2, there is depicted a container 20 with a bulk liquid specimen containing multiple analytes 22 and target analyte binding paramagnetic particles 24. Based on the ability to attract the paramagnetic particles via the application of a magnetic field thus serves as a basis for separating out such particles along with the bound analytes of interest; however, the prior art application of magnetic fields to such system is sub-optimal.

Figure 3:
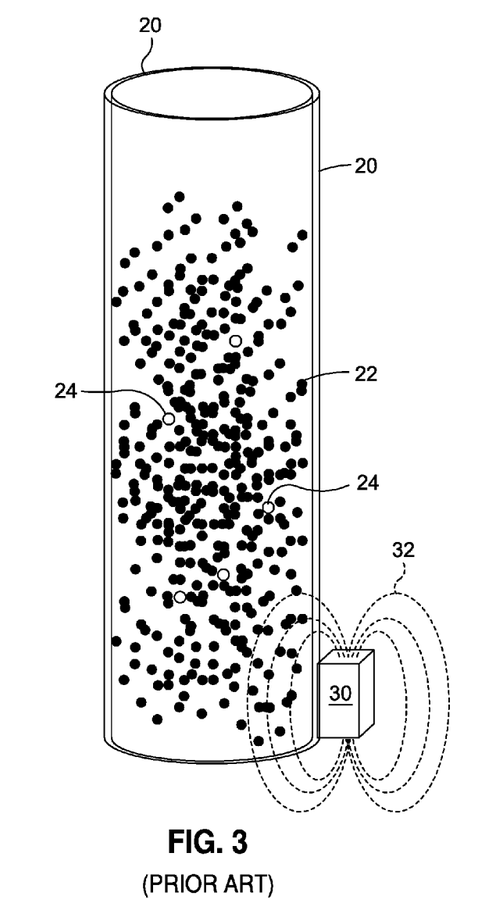
FIG. 3 illustrates the container of FIG. 2 with bulk fluid specimen containing multiple analytes and target analytes binding paramagnetic particles in proximity to a magnetic source producing a small magnetic flux.

With respect to FIG. 3, which utilizes a small magnet 30 producing a small static magnetic field 32 about a select area of the sample collection device 20, it is readily recognizable that focusing the target into a small area using a small static magnetic field is ineffective. Due to the exponential loss of magnetic field strength with distance from magnetic source, a small magnetic source, such as 30, cannot project a sufficient magnetic field 32 to penetrate the entire specimen. Such an approach relies on random diffusion of the target into attractive forces of the magnetic field 32. This approach is further disadvantaged by the necessity to transfer the target to a much smaller reaction vessel for subsequent analysis.

Figure 4:
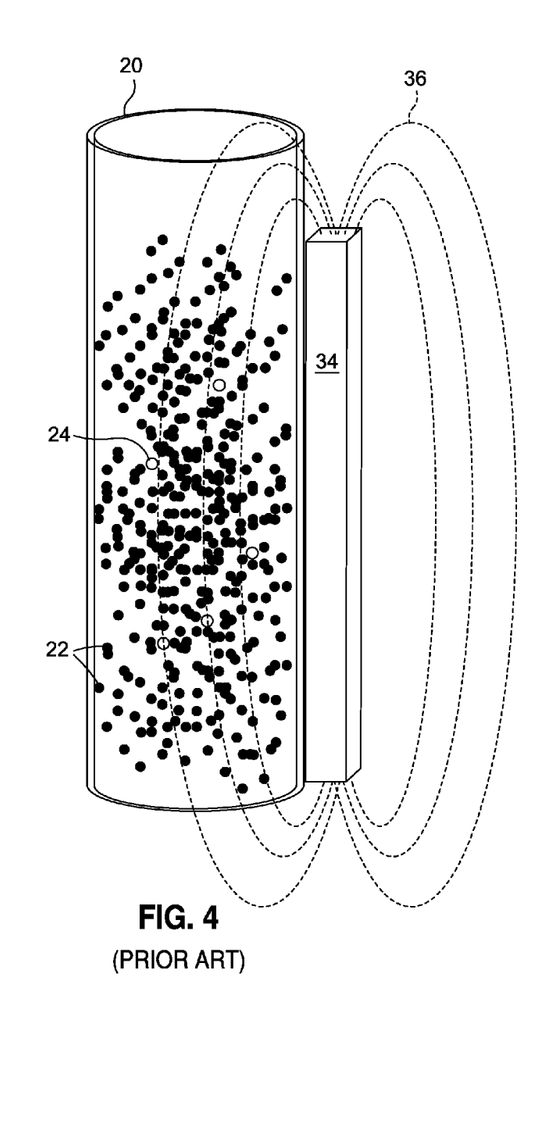
FIG. 4 illustrates the container of FIG. 2 with bulk fluid specimen containing multiple analytes and target analytes binding paramagnetic particles in proximity to a magnetic source producing a large magnetic flux.

Alternatively, as shown in FIG. 4, the use of a larger magnet 34 to produce a correspondingly larger magnetic field 36 that penetrates the entire volume of the specimen inherently draws target to a proportionately large capture area that complicates or thwarts attempts to consolidate rare targets such as 24 into a volume suitable for analysis chambers. In this regard, the magnetic field 36 and subsequent zone of capture has too great of a surface area to effectively isolate and concentrate the sought-after analyte 24.

Figure 5:
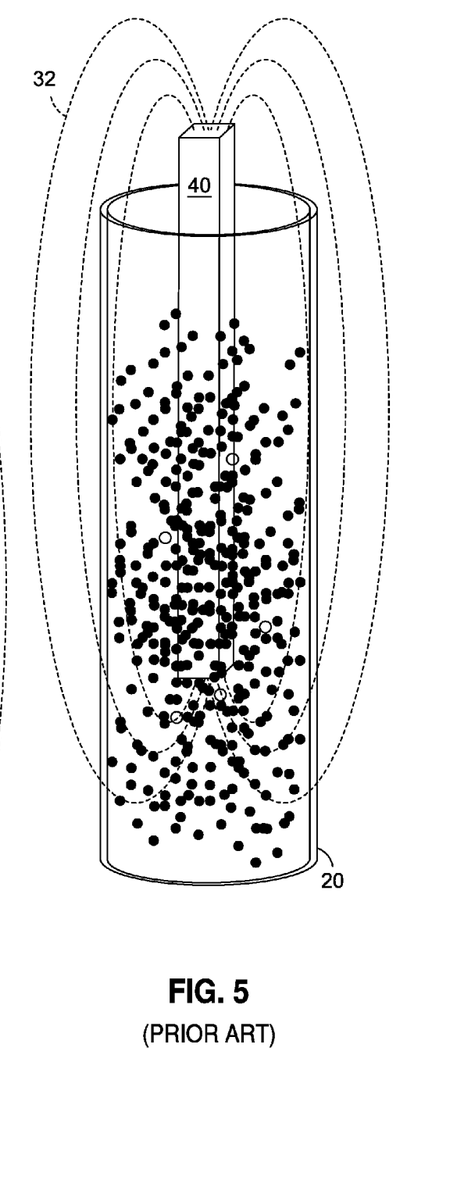
FIG. 5 illustrates the container of FIG. 2 with bulk fluid specimen containing multiple analytes and target analytes binding paramagnetic particles further having a magnetic source immersed therein producing a large magnetic flux.

Referring now to FIG. 5 there is shown a further magnetic separation technique whereby a magnetic source 40 is immersed into a specimen in order to increase the efficiency of the magnetic field 42 to attract the target analyte (i.e., biological macromolecule or cell) 24; however, the challenge of transferring the target 24 from the magnet 40 and resuspending the target analyte in a much smaller volume container can result in loss, damage and/or degradation of the target biological particle. To address this shortcoming, the prior art has relied upon elaborate mechanical sheath-type devices and methods whereby a sheath is placed between the magnetic source and the target such that said target is attached to the surface of the sheath which allows the magnet to be removed. Inevitably, this approach results in the target analyte being spread over a large surface area, which in turn requires removal of target analyte from the sheath using a wash volume, thus again creating a dilute solution of the analyte.

Even after the most effective techniques are used to enrich or maximize the concentration of the population of biological particles of interest in a given sample, the volume of the sample is still oftentimes far too large to allow for accurate and thorough investigation as to whether the particle is present, and much less to what degree. For example, from a 7.5 ml specimen sample, in order to perform PCR (i.e., polymerase chain reaction for analysis of short sequences of DNA or RNA), a 60× to 1500× volume reduction is required insofar as PCR is well-known to have a working volume 0.005 to 0.125 ml, and a maximum volume of 0.20 ml. Similarly, microscope slides typically have a working volume of approximately 0.002 to 0.007 mL and a maximum volume of 0.020 mL, and would require a 1071× to 3750× volume reduction of a 7.5 ml sample in order to reach a manageable volume. Still further, for tests performed in microwells, each microwell typically has a working volume of 0.075 to 0.200 ml, and a maximum volume of 0.36 ml. A 37.5× to 100× volume reduction would thus be required to make the sample suitable.

Accordingly, there is a substantial need in the art for systems and methods that can effectively detect, separate and isolate target analytes of interest, and in particular biological macromolecules and cells of interest that may be present in very low quantities whereby a large, bulk specimen or sample is both reduced in volume to an acceptable working volume and the target analyte of interest being concentrated or enriched therein. There is a further need for such systems and methods that can utilize magnetic and other enrichment methods so as to increase the concentration or presence of a target analyte of interest in a sample that is reduced from a first large or bulk volume to an acceptable working volume. Such improved systems and methods are further preferably of simple design, easy to operate, can produce highly accurate and reproducible results, are relatively inexpensive and time efficient to perform and exceptionally effective in detecting, separating and isolating target analytes of interest in a manner that minimizes sample loss and/or potential contamination or degradation of the target analyte.

BRIEF SUMMARY

The present invention specifically addresses and alleviates the above-identified deficiencies in the art. In this regard, the present invention is directed to a system and the use of that system to detect the presence of an analyte of interest within a liquid sample via the sequestration of the analyte of interest within a substantially reduced volume of the fluid sample, which in turn greatly facilitates the ability to detect the analyte compared to conventional means.

To achieve that end, there is provided a specimen chamber assembly that is operative to receive a bulk fluid sample and ultimately concentrate or enrich a target analyte of interest within a substantially reduced volume of the sample fluid. According to a preferred embodiment, the specimen chamber assembly comprises the combination of a bulk specimen reservoir that is operatively interconnectable with at least one vertex. Such components are preferably configured such that the reservoir has a greater volume than that of the at least one vertex attached thereto. Further provided is a magnetic capsule that is operative to engage with the vertex portion of the specimen chamber assembly and impart a magnetic field thereto. In this regard, the magnetic capsule is preferably designed to be axially positionable about the vertex so as to apply a magnetically attractive force into the interior thereof.

In use, a liquid specimen containing an analyte of interest is introduced into the bulk specimen reservoir, along with paramagnetic materials that are operative to selectively bind with the target analyte sought to be detected. In this regard, it is believed that the target analyte may take any of a variety of molecules, chemical substances, physical agents and the like, and in particular can include biological materials, and in particular biological macromolecules, cells, and the like, collectively referred to as biological particles.

The liquid sample with paramagnetic particles specific for the analyte of interest are introduced into the bulk specimen reservoir and the vertex subsequently interconnected thereto so as to define the specimen chamber assembly. In a preferred embodiment, a volume of air or other gas is captured within the specimen chamber assembly so as to facilitate the ability of the liquid specimen contained therein to be thoroughly mixed and allowed to thoroughly circulate throughout the interconnected specimen chamber assembly so as to sufficiently enable the paramagnetic particles to bind with the target analyte of interest. According to a preferred embodiment, the amount of air or gas allowed to remain within the specimen chamber can range from 10% to 50% of the total volume, and in a more highly preferred embodiment can range from 40% to 20%. In a most highly preferred embodiment, the amount of air to gas present in the specimen chamber assembly ranges from 25% to 35%. Concurrently with or following the mixing step, the magnetic capsule is interconnected with the vertex and is operative to impart magnetically attractive forces thereto to thus react, draw and sequester the paramagnetic materials within the vertex interior. By virtue of the magnetic attraction, a substantial portion, and preferably at least a majority of the paramagnetic materials, as well as the analyte of interest bound thereto, will be sequestered within the vertex. Moreover, by virtue of the reduced volume of the vertex relative to the bulk specimen reservoir, the amount of liquid specimen within which the sequestered paramagnetic particles (and hence the analyte of interest) is contained is substantially reduced relative to the total specimen volume introduced into the specimen chamber assembly. By reducing the volume, as well as enriching the presence of the target analyte of interest therein, the target analyte is consequently more easily and readily identified and quantified relative to prior art methods.

In further refinements of the invention, it is contemplated that two or more detachable vertices may be interconnectable with the specimen reservoir with each respective vertex being engageable with a dedicated magnetic capsule so as to facilitate the ability to sequester paramagnetic particles, and possibly detecting two or more dissimilar analytes of interest within a single fluid sample. Moreover, it is contemplated that depending on the type of analyte sought to be detected, modifications may be made to the amount of air or gas contained within the specimen chamber assembly, the type of gas used, e.g., 5% $CO_2$, the duration of mixing, the type of mixing and the intensity of such mixing, all of which may be selectively controlled. In addition, it is contemplated that certain reactions operative to facilitate the detection of an analyte of interest may be brought about within the specimen chamber assembly via the introduction of chemical additives, such as detergents, buffers, preservatives, catalysts such as enzymes, detection moieties plus numerous others well-known to those skilled in the art. Still further, to the extent desired, the specimen chamber assembly may be operatively subjected to thermal energy, such as heating, electromagnetic energy, including ultra-violet or infrared radiation, microwaves, and the like, and/or mechanical energy or forces, such as ultrasound, centrifugation and the like. Along those lines, the present invention contemplates that any force or energy as may be desired to facilitate mixing or to induce a desired reaction to facilitate: 1) the ability of an analyte of interest to ultimately react with a magnetic particle; and 2) become sequestered within a vertex may be deployed.

The invention presented herein thus provides a simple, universal, scalable system for sequestering rare targets dissolved, suspended or otherwise dispersed in large liquid volumes without reliance on complex work flows, precision fluidics, and excessive working times associated with prior art. The invention is useful for extending the lower limit of detection associated with prior art magnetic separation methods by greatly increasing the volume of specimen that may be easily processed at once using a single specimen chamber provided with a single vertex or plurality of vertices and focused magnetic field(s) external to said vertex or vertices. The invention can also be used in non-analytical applications to increase the efficiency of removing impurities from a bulk solution or to recover high value rare materials such as dispersed catalysts used in industrial processes.

BRIEF DESCRIPTION OF THE DRAWINGS

These and other features and advantages of the various embodiments disclosed herein will be better understood with respect to the following description and drawings, in which like numbers refer to like parts throughout, and in which.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

Figure 6:
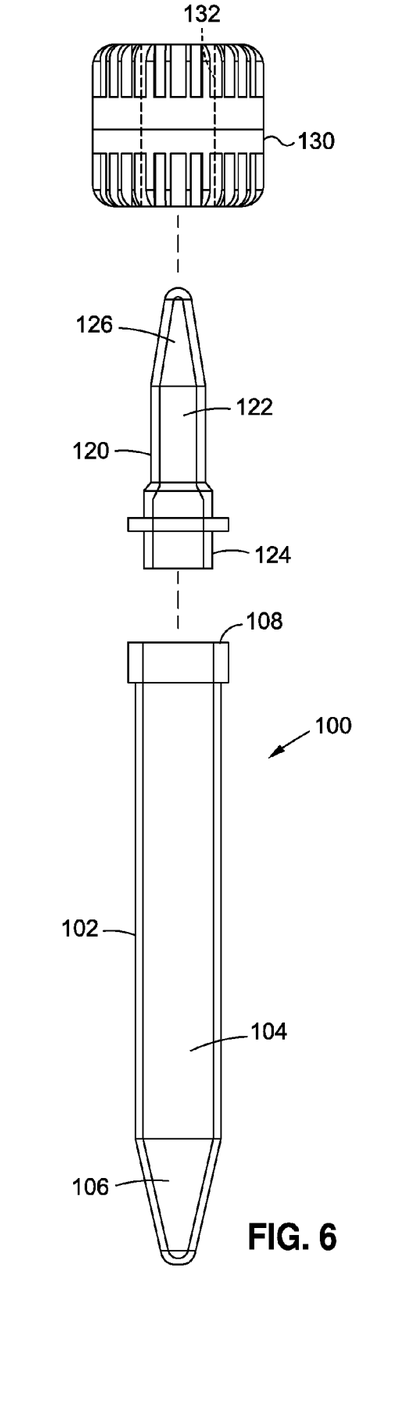
FIG. 6 is an exploded perspective view of exemplary components of the system of the present invention.

Referring now to FIGS. 6-12, and initially to FIG. 6, there is shown a system 100 for use in facilitating the detection, separation and isolation of a target analyte suspected of being present in a bulk fluid sample. Per the system 100, there is provided a bulk specimen reservoir 102 that is operative to interconnect with a vertex 120. The specimen reservoir 102 includes an interior 104 that defines a volume for receiving the bulk fluid sample. The specimen reservoir 102 further includes a proximal end 108 configured with a collar or other similar-type structure for interconnecting with the vertex 120, discussed more fully below. In the embodiment shown, the distal-most end 106 may be configured to have a generally frusto-conical configuration so as to facilitate the use of the specimen reservoir in other separation applications, such as centrifugation or precipitation reactions.

With respect to vertex 120, the same is provided with a proximal mating surface 124 operative to interconnect with 108 of the specimen reservoir 102. The vertex 120 further includes an interior portion 122 defining a volume that is less than that of the volume 104 defined within the interior of specimen reservoir 102. The distal-most end 126 of vertex 120 may also assume a frusto-conical configuration to help with further applications, such as centrifugation, for use in separating materials contained therein, also discussed more fully below.

The system 100 further includes a magnetic capsule 130 that includes at least one, and preferably a plurality of magnets radially disposed about an interior channel 132. In this regard, channel 132 is operative to axially receive vertex 120 and impart a magnetic flux into the interior thereof for use in facilitating the sequestration of a target analyte of interest via the use of paramagnetic particles discussed more fully below.

While depicted as having conventional test tube structures, it should be understood that specimen reservoir 102 and vertex 120 interconnectable therewith may take any of a variety of shapes and sizes and need not necessarily take the cylindrical structures as shown. In this regard, so long as the vertex is designed to have a smaller interior volume than that of specimen reservoir 102 and further is operative to engage with a magnetic capsule 130 such that the latter can impart a magnetic flux thereto, all variations on shapes and sizes should be considered to be well within the skill level of the ordinary artisan. Moreover, it is contemplated that the system 100 may include two or more vertices that can interconnect with bulk specimen reservoir 102 at different locations as may be desired to separate dissimilar analytes and/or sequentially sequester one or more target analytes as may be desired. Likewise, it is understood that the materials utilized to fabricate the components, 102, 120 and 130 of system 100 may take any of a variety well-known in the art, which can include certain plastics, glassware and the like as may be well-suited for a particular separation application. Again, the choice of materials for use in a particular application is well within the skill of the ordinary artisan.

Figure 7:
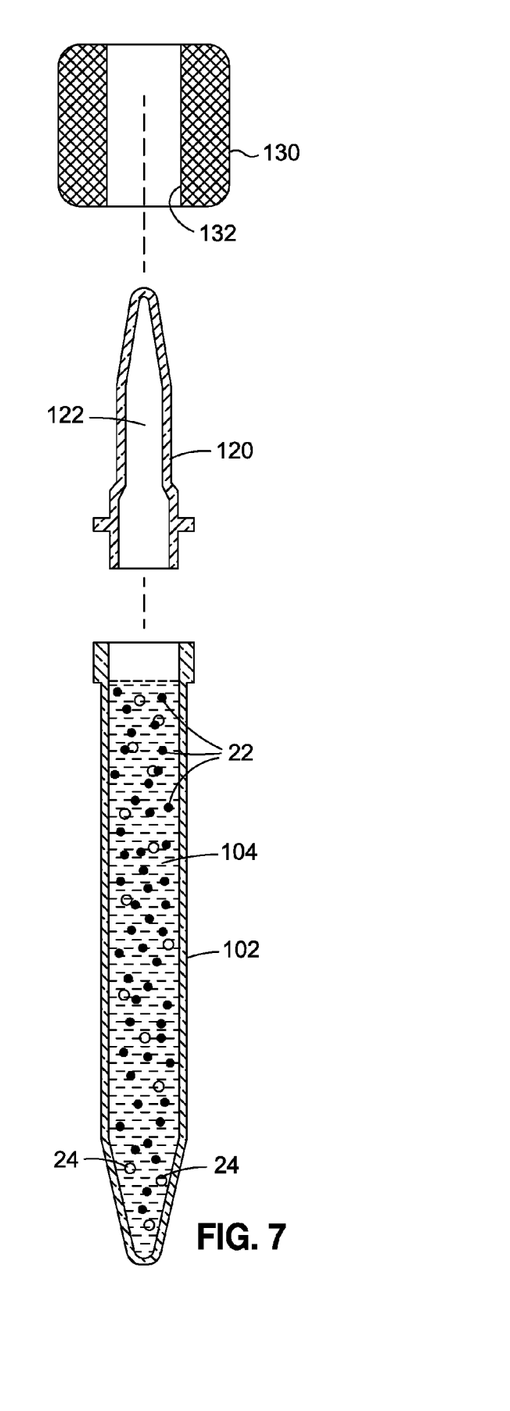
FIG. 7 is an exploded cross-sectional view of the system components of FIG. 6 having a bulk fluid specimen disposed within the bulk specimen reservoir component thereof.

Referring now to FIG. 7, there is shown the use of the system 100 in the initial step of a process for separating a target analyte of interest suspected of being present in a bulk fluid sample. As illustrated, a fluid specimen containing multiple analytes 22 is received within bulk specimen reservoir 102. Additionally included are paramagnetic materials that are operative to bind with a target analyte suspected of being present within the fluid sample. The use of magnetic particles and the ability to design the same such that such particles specifically bind with a target analyte of interest are well-known and readily understood in the art, as discussed in the Background, and includes any and all mechanisms, such as the use of ligands, receptors, chelate, bonding partner and any other mechanism known in the art to facilitate the formation of a complex between the paramagnetic particles and the target analyte. The complex formed by a paramagnetic particle and the target analyte of interest via a ligand is represented by 24 in Figures as shown.

Such bulk sample may take any of a variety of liquid samples that might include a target analyte sought to be detected and, if desired, subsequently separated and isolated. Accordingly, it should be understood that the target analyte might include any type of molecule, particulate, substance, and the like. It is particularly contemplated that the analyte of interest, coupled to the paramagnetic particle 24 will include biological macromolecules, such as segments of DNA, RNA, proteins, peptides, intracellular structures, specific types of cells such as cancer cells and the like, all of which are collectively referred to as biological particles. In this regard, it is contemplated that the system 100 and the methods of using the same will be particularly well suited for life science applications wherein specific types of rare biological particles are sought to be detected that are otherwise significantly difficult to find.

FIG. 7 further depicts the positioning and orientation of the vertex 120 engageable with the bulk specimen reservoir 102 once the bulk fluid sample is received therewithin.

Figure 8:
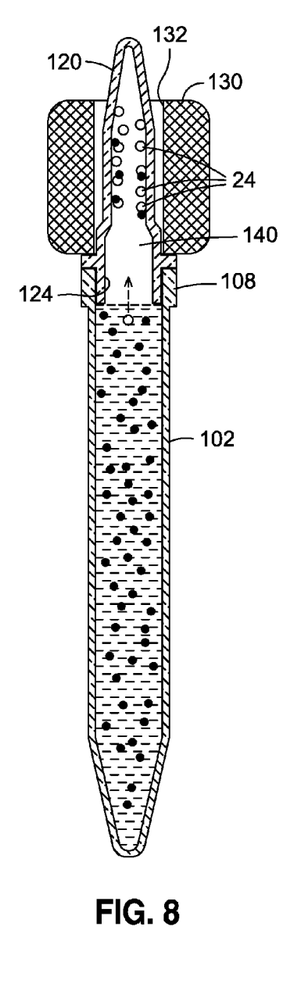
FIG. 8 is a cross-section view of the system components of FIG. 7 wherein the components are operatively interconnected with one another for testing a bulk fluid sample.

Importantly, by virtue of the interconnection between the vertex 120 and specimen reservoir 102, a volume of air or gas, contained within the interior 122 of vertex 120 will be introduced into the specimen chamber once those components 102, 120 are interconnected. Presently, it is believed that the volume of air captured within the specimen chamber, defined by the interior volumes 122 and 104 as depicted in FIG. 8, will be present in an amount ranging from 10% to 50% of the total volume of the specimen chamber. In a more highly preferred embodiment, the air/gas will be present in the range from 20% to 40% of the total volume, and in a most highly preferred embodiment ranges from 25% to 35% of the total volume. In this regard, inclusion of the space for air and/or gas is crucial to allow for adequate mixing within the specimen chamber so as to allow the paramagnetic materials with analyte of interest bound thereto to fully circulate throughout the specimen chamber and ultimately be subjected to the magnetic field imparted by magnetic capsule 130, discussed more fully below. Likewise, the type of air and/or gas left to fill the remaining volume of the specimen chamber assembly when the specimen reservoir 102 is interconnected with the vertex 120 may be selectively chosen for a particular application. For example, inert gasses such as nitrogen or helium may be utilized in certain applications where risk of oxidation could occur to the analyte of interest sought to be detected. The types and volumes of gasses thus utilized are believed to be within the realm of one of ordinary skill.

As will be readily understood by those skilled in the art, depending on the particular type of target analytes sought to be detected, numerous parameters and adjustments may be made to facilitate the ability of the paramagnetic materials to bind to the target analyte of interest and/or facilitate the ability of the target analyte to be more easily and readily detected via the interaction with the paramagnetic particles. To that end, it should be understood that the bulk fluid sample introduced into the specimen reservoir 102 as shown in FIG. 7 may additionally be mixed with other materials, such as chemical agents, additives, detergents, buffers, preservatives, catalysts (such as enzymes and the like), one or more detectable moieties and/or complexing agents as may be suited for a particular test or for the detection of a particular analyte.

It will further be appreciated that the magnetic capsule 130 will also be designed to impart a magnetic flux or field sufficiently about the vertex 120, discussed more fully below, so as to create a magnetic force strong enough to interact, attract and sequester the magnetic particles bound to the analyte of interest 24. To that end, it is believed that a wide variety of magnet arrangements can readily be designed by one of ordinary skill in the art whereby magnetic elements disposed within magnetic capsule 130 are oriented to direct a magnetic field within the interior 122 of vertex 120. For example, it is contemplated that a series of magnetic elements may be radially disposed about magnetic capsule 130 and oriented such that the poles thereof impart the desired magnetic field into the interior 12 of vertex 120. It is further contemplated that a variety of ring-type magnets and magnets having multiple pole orientations may be utilized to impart the desired and necessary degree of magnetic force to attract and sequester the magnetic particles complexed to the target analyte of interest 24. To that end, it is contemplated that the types of magnets, the magnetic strength of the magnets, the orientation of the magnets relative to the interior dimensions 122 of vertex 120, the viscosity of the fluid sample being tested and the type and concentration of the paramagnetic particles used for a particular application all will be selectively chosen to attain an optimal degree of detection of the analyte of interest 24.

Referring now to FIG. 8, there is shown the vertex 120 as interconnected with the bulk specimen reservoir 102. The interconnection between the vertex 120 and specimen reservoir 102 defines a specimen chamber assembly as shown. In such configuration, the fluid sample containing both analytes and the paramagnetic: target analyte complex 24 is allowed to freely circulate within the combined interior portions 104 and 122 of the interconnected components, 102, 120. While in such configuration, the magnetic capsule 130 is axially positioned over vertex 120 via insertion of the vertex 120 through axial opening 132, as shown. Based on their proximity, the magnetic elements disposed within magnetic capsule 130 selectively impart a magnetic flux that is operative to retain the paramagnetic particle: target analyte complex 24 as shown. In this regard, by virtue of the attraction between the magnet field and the magnetic particles, a substantial portion, and preferably at least a majority of such particles having the analyte of interest bound thereto 24 will be sequestered within the vertex 120.

As will be readily appreciated by those skilled in the art, in order to retain the paramagnetic materials within vertex 120, it is contemplated that the interior of the vertex 120 may be surface treated with receptors, certain materials and the like to thus enable the paramagnetic materials to remain sequestered once magnetically attracted thereto. Other modifications will also be readily understood by those skilled in the art that could possibly facilitate the ability of the paramagnetic materials to remain within vertex 120 once attracted thereto via the action of magnetic capsule 130.

Figures 9, 10:
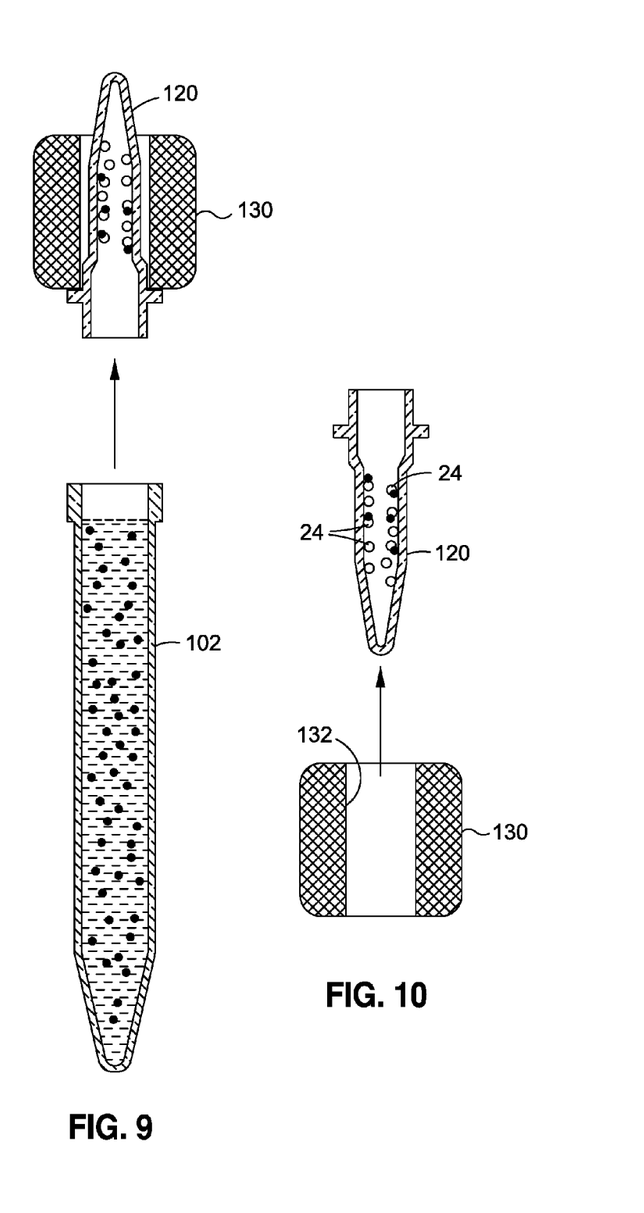
FIG. 9 is an exploded cross-sectional view of the system components of FIG. 8 wherein a portion of target analytes present in the bulk fluid sample are shown separated and magnetically retained within the vertex component via the attached magnetic capsule of the system.
FIG. 10 is an exploded cross-sectional view of the vertex and magnetic capsule of FIG. 9 illustrating removal of the vertex from the magnetic capsule.

Once sufficiently contained within vertex 120, the paramagnetic particles having the analyte of interest bound thereto 24 will continue to be sequestered therein so long as magnetic capsule 130 is operative to impart the retaining magnetic field, as shown in FIG. 9. When in such configuration, the vertex 120 may be removed from the bulk specimen reservoir 102 to thus substantially remove the analyte of interest from the bulk specimen liquid. The retained analyte of interest 24 captured within the vertex 120 may then be further separated and isolated by removing the magnetic capsule 130 and enabling the target analyte to be resuspended in a minimum volume of fluid or processed dry depending on the specific application, as shown in FIG. 10.

A further aspect of the present application believed to be significant in obtaining optimum results includes various considerations regarding possible incubation times, mixing intervals, mixing intensity and application of mechanical, thermal and/or electromagnetic energy to the specimen chamber assembly so as to not only enhance the ability of the paramagnetic materials to bind to the target analyte of interest, but also enable the complex formed by the paramagnetic material and analyte of interest 24 to circulate within the specimen chamber assembly and ultimately be subjected to the retaining magnetic forces imparted by magnetic capsule 130. To that end, and as discussed above, numerous agents may be added to the bulk liquid specimen along with the paramagnetic particles so as to maximize the potential that a given target analyte may be detected. For example, to the extent a specific biological particle, such as an organelle or specific type of segment of DNA is sought to be identified, detergents and digestive enzymes may be deployed so as to facilitate the ability of a specimen containing cells to lyse or otherwise become digested so that intracellular structures and macromolecules can be accessed. Similarly, as discussed above, the volume of air remaining within the specimen chamber assembly may be selectively chosen so as to facilitate a higher or lesser degree of mixing, and hence circulation of the paramagnetic materials into and out of the interior 122 of vertex 120.

Still further, it is contemplated that mechanical energy, such as ultrasound, thermal energy, such as heat or refrigeration, and electromagnetic energy, such as ultra-violet or infrared radiation, microwaves and the like, may be selectively deployed so as to facilitate a reaction within the specimen chamber assembly or otherwise enhance the ability of the paramagnetic particles to interact with the magnetic forces provided by magnetic capsule 130.

Figure 11:
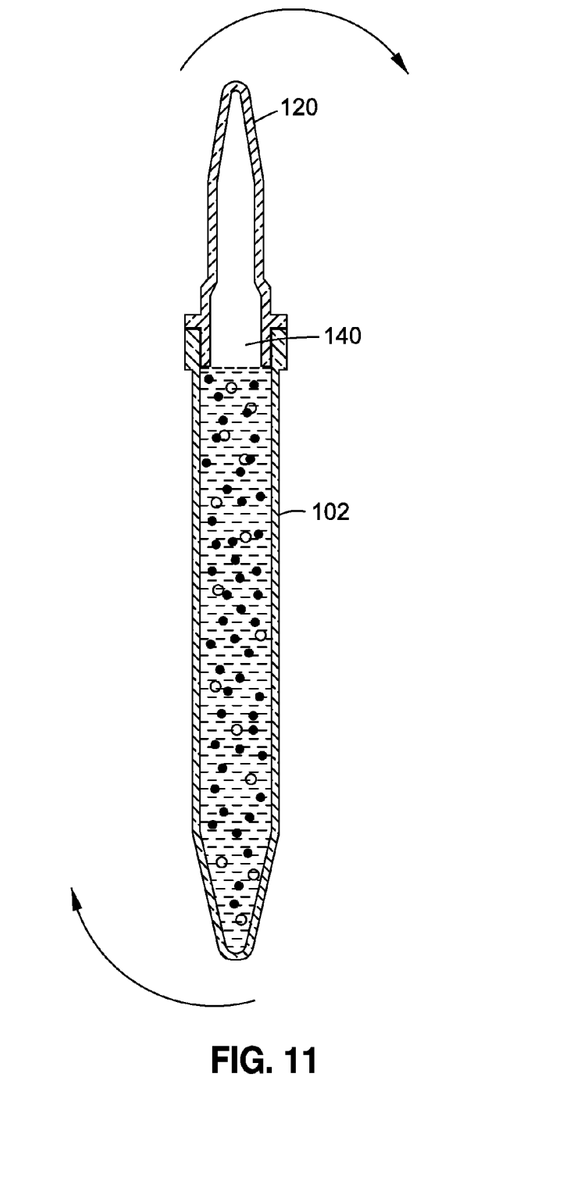
FIG. 11 is the cross-sectional view of FIG. 8 furthering illustrating the specimen chamber containing specimen in rotational motion during a mixing interval.
Figure 12:
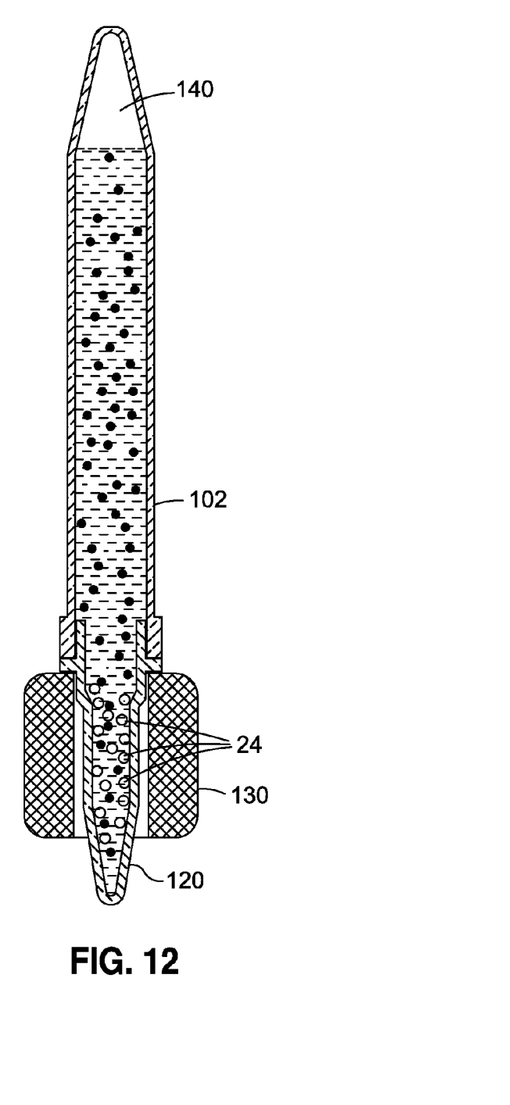
FIG. 12 the cross-sectional view of FIG. 11 illustrating the interconnected specimen chamber and magnetic capsule assembly with specimen in motion during a target sequestering interval.

To that end, and as shown in FIGS. 11 and 12, if a mixing interval is required to assure binding complex formation of the target analyte and binding paramagnetic particles, the specimen chamber assembly may be set in motion in a manner that liquid and air contained within the specimen chamber assembly ultimately fill the vertex part of the specimen chamber. As illustrated, the specimen chamber assembly defined by the interconnection of the bulk specimen reservoir 102 and vertex 120 may be rotated in a clockwise manner shown in FIG. 11 to assume the inverted configuration of FIG. 12. As should be readily understood by those skilled in the art, however, the motion of the specimen chamber assembly can take any of a variety of forms, including rocking, shaking, compression, separate from or in addition to the rotational motion as shown, or may include combinations of such movements as may be desired for a particular application. Indeed, it is expressly contemplated that some mixing activity must necessarily occur to ensure that liquid and air contained within the specimen chamber assembly enables both liquid and air to alternately fill the interior 122 of vertex 120 and consequently enable the magnetic forces of the magnetic capsule 130 to impart the sequestering effect. Likewise, such mixing activity, whether it be rotational, rocking, shaking, compression or combinations thereof, will necessarily cause liquid to recede from the vertex 120 and subsequently be replaced by air and/or gas, which in turn removes the surface tension of the liquid and any unbound background analytes 22 that may interfere with the detection of the desired complex of the paramagnetic particle and analyte of interest 24.

Still further, it is contemplated that the degree and type of mixing will be selectively chosen for a particular application, and may involve mixing just the specimen with paramagnetic particles within the specimen chamber assembly for a first duration without any application of the magnetic field as imparted by the magnetic capsule 130, which may be allowed to continue for a given duration and intensity sufficient to first enable the paramagnetic particles to sufficient form complexes with the target analyte of interest and, once such reaction has been substantially accomplished, then the magnetic capsule 130 may then be introduced to selectively apply the magnetic field within the interior of vertex 120 to accomplish the sequestering effect discussed herein. In this regard, it is contemplated that the systems and methods by which they are used can be sequentially used to perform a first paramagnetic particle mixing step followed by a second sequestering step.

As discussed above, it is contemplated that the systems and methods of the present invention may find widespread application in detecting any of a variety of target analytes, and especially target analytes that are present in trace amounts and normally difficult to detect using prior art methods. Numerous clinical and industrial applications are contemplated, including but not limited to diagnostic applications, such as the detection of cancer cells, specific types of antigens, pathogens and the like; detection of contaminants and pollutants in aqueous systems and food sources; purification of liquids; manufacturing and processing of various hydrocarbons, among others.

An example illustrative of the utility of the present invention will be readily appreciated in the context of cancer diagnosis. In this regard, the treatment and management of cancer patients increasingly relies on the doctrine of precision medicine. Instead of treatments based upon population averages, disease treatment and prevention takes into account individual variability in genes. Hence this doctrine examines the underlying genes and gene expression causative to the cancer and predicts optimal treatment and management of the patient. Since cancer is a disease that is organ or tissue specific, the analytic validity of genetic test results is based upon the presumption that the test result is traceable to a specific cell type originating from a specific organ or tissue.

Whenever possible, it is desirable to assess aforementioned individual genetic variability using so called liquid biopsy methods to evaluate body fluids for the presence of tumor cells. Liquid biopsy methods employ minimally invasive sampling techniques that typically do not involve surgical procedures to remove a sample of body tissue. For example, body fluids such as blood, urine, saliva, cerebral spinal fluid, pleural fluids, and others may be collected with minimal risk or trauma to the patient compared to surgical procedures. This is advantageous because these fluids replenish, are readily available, and provide an ideal methodology for surveillance of disease. As such, liquid biopsy methods can enable the development of convenient modes of early detection (screening), and surveillance of disease progression or regression in response to treatment.

A limitation of liquid biopsy methods is the reliance on the rare presence of tumor cells in these body fluids. Also, the target cell of interest is typically present in body fluids that contain a comparatively high number and variety of non-diagnostic background cells that are not relevant to diagnosis and mask the existence of the target cell. Early disease detection or minimal residual disease detection in many instances is not feasible because the relative number of target cells is below the lower detection limit of prior art. This may be remedied in some applications by collecting a larger specimen of body fluid, however, prior art attempts at using large volume specimens are cumbersome, lack robustness, are costly, difficult to automate, and are not conducive to commercialization on a large scale. It is an objective of this invention to sequester target analytes from a bulk volume of specimen whose total volume includes a liquid volume and a solid volume, such as the liquid and cellular components that comprise the total volume of many biological fluids. A specific application for this purpose is provided:

Example 1

Circulating Tumor Cells in 15-30 milliliters of human whole blood. A 60 mL specimen chamber assembly is provided via the interconnection between a bulk specimen chamber 102 having an interior volume of 58 mL and a vertex 120 having an interior volume of 2 mL.

After removal of the vertex 120, 15-30 mL of whole blood is introduced into the bulk specimen reservoir 120. 15 to 30 mL of blood containing between 75 and 150 billion cells is deposited into the bulk specimen reservoir 102 followed by 20 mL of liquid reagent consisting of buffer, conditioners, chemical agents and a suitable number of target cell specific paramagnetic particles. For example, an average total combined liquid volume of 42.5 mL occupying 71% of specimen chamber assembly total volume (SCV) with a total liquid volume can range from 35 mL (58% SCV) to 50 mL (83% SCV). This in turn creates an average air space of 17.5 mL (29% SCV) and air space range from 25 to 10 mL (42% to 17% SCV) inside the specimen chamber assembly.

Regarding the liquid reagent composition, buffer can be any suitable buffer, typically in the pH range between 6 and 8.5. Conditioners and chemical agents may include: salts, metal ions, sugars, amino acids, antibiotics, anticoagulants, anti-foaming agents, surfactants, fixatives and many other conditioners or combinations thereof commonly deployed in tissue culture, immunochemistry, cytology, pathology, and hematopathology. Paramagnetic particle numbers may range from several thousand to several billion and are included within the total volume of liquid reagent, whether added separately or concurrently with the other liquid reagent components.

Subsequent to specimen and liquid reagent additions to the bulk specimen reservoir 102, the specimen chamber assembly is then reassembled by replacing the detachable vertex 120 as in FIG. 7 to form the specimen chamber assembly.

The specimen chamber assembly is mounted on a horizontal rotational device and set in rotational motion at a rate to cause mixing sufficient to form complexes between the target cells and the target cell-specific paramagnetic particles. The duration of the mixing interval should be sufficient to allow a majority of target cells to be bound by target cell specific paramagnetic particles.

Upon conclusion of the mixing interval, a magnetic capsule 130 is mounted to the vertex component 120 of the specimen chamber assembly. This can be accomplished while maintaining rotational motion or by briefly interrupting rotational motion to allow mounting of the magnetic capsule 130 to the vertex 120 while stationary.

After mounting magnetic capsule 130 the system continues its rotational motion for a duration sufficient to allow a majority of target cell/target specific magnetic particle complexes to be sequestered in the vertex component 120 of the specimen chamber assembly by the magnetic field produced by the magnetic capsule 130.

Upon completion of the sequestering duration, rotational motion is halted and the entire system assembly is removed from the rotational device. The specimen chamber assembly is held in a vertical position for a duration sufficient to allow a majority of liquid to drain from the vertex 120. Once drained, the vertex/magnetic capsule assembly 120/130 is detached and inverted to allow removal of the vertex 120 from the magnetic capsule 130 without loss of target cells. The target cells can then be resuspended in any appropriate working volume for as appropriate for microscopy, PCR, sequencing and other types of analysis.

Separate and apart from CTC applications, the systems and methods of the present invention may be deployed to detect cancer calls present in urine. To that end, it is well known to those practiced in the field of urine cytology that voided urine may contain an unpredictable number (if any) of cancer cells exfoliated from kidney, bladder, prostate, urethra, and other tissues. Unlike blood, urine total cell counts can range from a few cells to many billion if hematuria is present. In addition to exfoliated target cells from aforementioned organs and body tissues, urine specimen components can include blood cells (a condition known as hematuria), bacteria, large amounts of mucus, crystals, and sperm. As a result, the challenge of detecting low grade lesions varies between 26% and 45% (Laucirica, R., et. al. Arch Pathol Lab Med. Vol 134, January 2010. It has also been reported that the diagnostic accuracy of detecting urinary tract malignancies as a whole increases from 50% to 75-90% by assessing larger urine volumes and multiple urine voids (ref: Elsheikh, T, Cleveland Clinic presentation, URL: https://www.ahn.org/sites/default/files/file/elsheikh-2.pdf). Clinical studies have also shown that nucleic acid amplification test sensitivity for detecting *Chlamydia trachomatis* improved as the volume of first-catch urine specimen increased (Moncada, J., et. al. Journal of Clinical Microbiology. October 2003, p 4848-4843.

The volume of voided urine can vary widely between individuals and within individuals. Urine volume may also be determined per void or per 24 hour period. The normal range for a 24 hour urine void is 800 to 2000 milliliters (mL) while the average volume per void ranges from 210 to 346 mL of men 50-54 years of age. See, e.g., Blanker, M., et. al. Voided Volumes: Normal Values and Relation to Lower Urinary Tract Symptoms in Elderly Men, A Community Based Study. Urology 57(6), 2001. As a result of those volumes, target analytes, such as exfoliated cells can be very difficult to detect. How such shortcomings may be overcome by an application of the present invention is provided in the following specific example:

Example 2

Isolation of target cells from urine followed by isolation of DNA from the same urine specimen.

Figure 13:
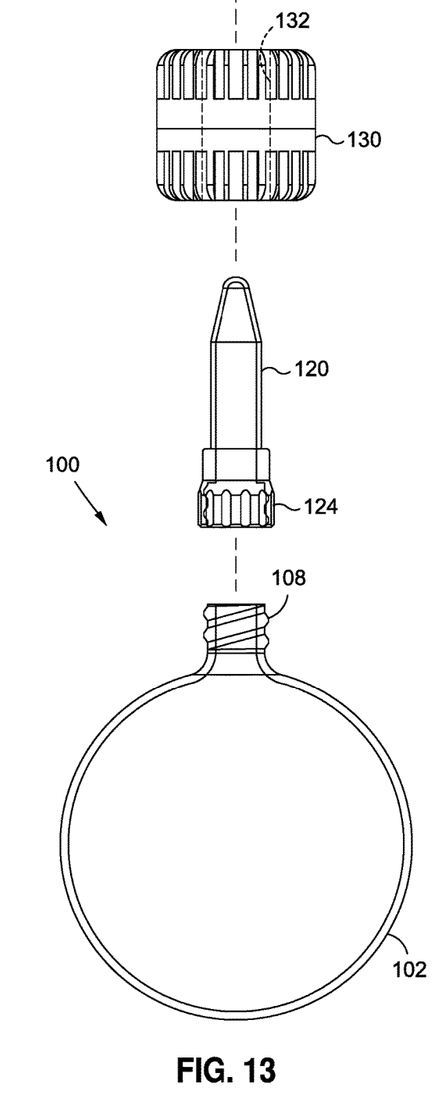
FIG. 13 is an exploded perspective view of exemplary components of a second embodiment of the system of the present invention.
Figure 14:
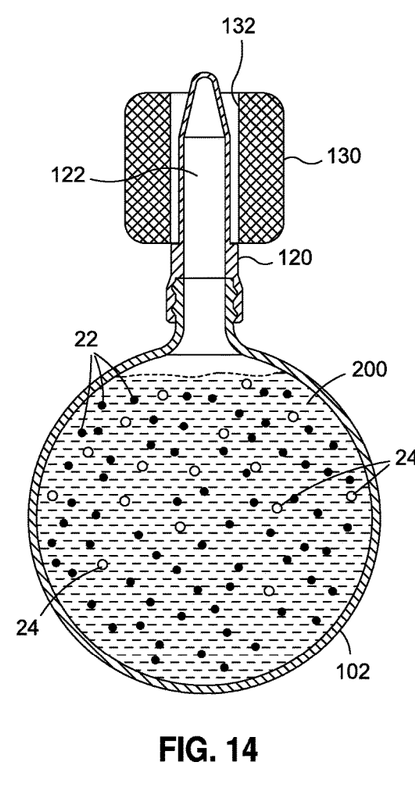
FIG. 14 is a cross-sectional view of the system components of FIG. 13 wherein the components are operatively interconnected with one another for testing a urine fluid sample.

Referring now to a 350 mL specimen chamber assembly having a bulk specimen reservoir volume of 345 mL and a vertex volume of 5 mL. To facilitate the ability to collect and test a specimen of such volume, it is contemplated that in addition to the designs depicted above and other variations thereof that would be readily understood by those skilled in the art, there is shown in FIGS. 13 and 14 a further exemplary embodiment. As shown in the exploded view of FIG. 13, system components bulk specimen reservoir 102, vertex 120 and magnetic capsule 130 are provided and operatively interconnectable such that the distal end 108 of bulk specimen reservoir 102 may be threadedly interconnected with distal-end 124 of vertex 120. As per the other embodiments discussed above, the interconnection between the vertex 120 and bulk specimen reservoir 102 cooperate to define a specimen chamber assembly, as shown in the cross-sectional view of FIG. 14 with such parts interconnected. By virtue of the body of the bulk specimen reservoir having a generally spherical shape, the bulk specimen reservoir 102 is thus able to accommodate greater sample volumes as would be ideal for specimens such as urine, as opposed to smaller volume samples, such as those associated with blood testing, as discussed above.

Per the other embodiments discussed above, the magnetic capsule 130 is provided with an annular aperture 132 so as to be axially received about vertex 120, as shown in FIG. 14. Per the embodiments discussed above, magnetic capsule 130 is operative to project a magnetic field within the interior of vertex 120 such that when paramagnetic particles with target analyte of interest bound thereto circulate through interior 122 of vertex 120, such materials will remain sequestered therein.

After removal of the vertex 120, 200 mL of urine 200 is introduced into the bulk specimen reservoir containing an unknown number of cells, bacteria, mucus, and other background components. The specimen addition is followed by 50 mL of liquid reagent consisting of buffer, conditioners, chemical agents and a suitable number of target cell specific paramagnetic particles 24. For example, an average total combined liquid volume of 250 mL occupying 71% of specimen chamber assembly total volume (SCV). This in turn creates an average air space of 100 mL (29% SCV) inside the specimen chamber assembly.

Regarding the liquid reagent composition, buffer can be any suitable buffer, typically in the pH range between 6 and 8.5. Conditioners and chemical agents may include: salts, metal ions, sugars, amino acids, antibiotics, anticoagulants, anti-foaming agents, surfactants, fixatives and many other conditioners or combinations thereof commonly deployed in tissue culture, immunochemistry, cytology, pathology, and hematopathology. Paramagnetic particle numbers may range from several thousand to several billion and are included within the total volume of liquid reagent whether added separately or concurrently with the other liquid reagent components.

Subsequent to specimen and liquid reagent additions to the bulk specimen reservoir, the specimen chamber assembly is then reassembled by replacing the detachable vertex as in FIG. 14. No magnetic capsule is added to the specimen chamber assembly at this time.

The specimen chamber assembly defined by the interconnected bulk specimen reservoir 102 and vertex 120, is mounted on a horizontal rotational device and set in rotational motion at a rate to cause mixing sufficient to form complexes between the target cell and the target cell specific paramagnetic particle. The duration of the mixing interval should be sufficient to allow a majority of target cells to be bound by target cell specific paramagnetic particles.

Upon conclusion of the mixing interval the magnetic capsule is mounted to the vertex 120 component of the specimen chamber assembly. This can be accomplished while maintaining rotational motion or by briefly interrupting rotational motion to allow mounting of the magnetic capsule to the vertex while stationary.

After mounting magnetic capsule 130, the system assembly continues its rotational motion for a duration sufficient to allow a majority of target cell/target specific magnetic particle complexes to be sequestered in the vertex component of the specimen chamber assembly by the magnetic field produced by the magnetic capsule.

Upon completion of the sequestering duration, rotational motion is halted and the entire system is removed from the rotational device. The system is held in a vertical position for a duration sufficient to allow a majority of liquid to drain from the vertex. Once drained, the vertex 120/magnetic capsule 130 assembly is detached and inverted to allow removal of the vertex 120 from the magnetic capsule 130 without loss of target cells. The target cells can then be resuspended in any appropriate working volume for as appropriate for microscopy, PCR, sequencing and other types of analysis.

Follow on Isolation of DNA:

Subsequent to the removal of target cells from the urine specimen 200 it may also be desirable to sequester DNA from the same specimen for the detection of sexually transmitted micro-organisms.

A volume of DNA binding paramagnetic particles sufficient to bind an adequate amount of DNA for PCR is added to the target cell depleted specimen. The paramagnetic particles may be sufficiently concentrated to have no appreciable volume effect on the system. These particles are readily available many manufacturers.

The specimen chamber assembly is then reassembled by replacing the detachable vertex 120. No magnetic capsule 130 is added to the specimen chamber assembly at this time.

The specimen chamber assembly is mounted on a horizontal rotational device and set in rotational motion at a rate to cause mixing sufficient to form complexes between DNA and the DNA binding paramagnetic particle. The duration of the mixing interval should be sufficient to allow a majority of target cells to be bound by target cell specific paramagnetic particles.

Upon conclusion of the mixing interval, the magnetic capsule 130 is mounted to the vertex 120 of the specimen chamber assembly. This can be accomplished while maintaining rotational motion or by briefly interrupting rotational motion to allow mounting of the magnetic capsule to the vertex while stationary.

After mounting the magnetic capsule 130 the system assembly continues its rotational motion for a duration sufficient to allow a majority of DNA/DNA binding paramagnetic particle complexes to be sequestered in the vertex 120 of the specimen chamber assembly by the magnetic field produced by the magnetic capsule 130.

Upon completion of the sequestering duration, rotational motion is halted and the entire system assembly is removed from the rotational device. The system is held in a vertical position for a duration sufficient to allow a majority of liquid to drain from the vertex. Once drained, the vertex/magnetic capsule assembly is detached and inverted to allow removal of the vertex from the magnetic capsule without loss of DNA bound paramagnetic particles. The DNA can then be resuspended in any appropriate working volume for use as appropriate for PCR, sequencing and other types of analysis.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed:

1. A method for sequestering a target analyte believed to be present in a bulk liquid specimen, said method comprising the steps:
   a. providing a bulk specimen reservoir defining an interior for receiving said bulk liquid specimen and depositing said bulk liquid specimen within said interior of said bulk specimen reservoir;
   b. contacting said bulk liquid specimen with a plurality of paramagnetic particles operative to selectively bind with said target analyte of interest to the extent said analyte of interest is present;
   c. providing a vertex having an internal volume, said vertex being detachably interconnectable with said bulk specimen reservoir containing said bulk liquid specimen and said paramagnetic particles in step b) such that said bulk liquid specimen with paramagnetic particles and any analytes of interest bound thereto is operative to flow and circulate within the interior of said at least one vertex;
   d. providing a magnetic capsule detachably interconnectable with said vertex when said vertex is interconnected to said bulk specimen reservoir in step c), said magnetic capsule being interconnected to said vertex so as to project a magnetic field within the interior of said vertex;
   e. sufficiently circulating said bulk liquid specimen with said paramagnetic particles and any analytes of interest bound thereto within the interior of said vertex while said magnetic capsule is coupled therewith for a duration sufficient to retain a majority of said paramagnetic particles within the interior of said vertex;

f. detaching said vertex from said bulk specimen reservoir following step e);

g. disengaging said magnetic capsule from said vertex detached in step f); and h. analyzing said paramagnetic particles retained within said vertex to determine the presence of said target analytes of interest.

2. The method of claim 1 wherein said analyte of interest is a biological particle.

3. The method of claim 2 wherein said biological particle is selected from the group consisting of macromolecules, proteins, peptides, intracellular structures, and cells.

4. The method of claim 3 wherein said cells are cancer cells.

5. The method of claim 3 wherein said bulk liquid specimen with said plurality of paramagnetic particles is circulated via a method selected from the group consisting of rocking, shaking, rotating and compressing.

6. The method of claim 3 wherein said bulk liquid specimen containing said plurality of paramagnetic particles is further subjected to electromagnetic energy to facilitate binding of paramagnetic particles to said target analyte of interest, if present, and retention of said paramagnetic particles within said interior of said vertex, said electromagnetic energy being selected from the group consisting of UV radiation, infrared radiation, and microwaves.

7. The method claim 3 wherein said bulk liquid specimen containing said plurality of paramagnetic particles is subjected to heating to facilitate binding of paramagnetic particles to said target analyte of interest, if present, and retention of said paramagnetic particles within said interior of said vertex.

8. The method claim 3 wherein said bulk liquid specimen containing said plurality of paramagnetic particles is subjected to cooling to facilitate binding of paramagnetic particles to said target analyte of interest, if present, and retention of said paramagnetic particles within said interior of said vertex.

9. The method of claim 3 wherein said bulk liquid specimen containing said plurality of paramagnetic particles is subjected to mechanical energy to facilitate binding of paramagnetic particles to said target analyte of interest, if present, and retention of said paramagnetic particles within said interior of said vertex.

10. The method of claim 9 wherein said mechanical energy is ultrasound.

* * * * *